United States Patent [19]

Crossley

[11] Patent Number: 4,703,044
[45] Date of Patent: Oct. 27, 1987

[54] IMIDAZOQUINOLINES CONTAINING OTHER HETEROCYCLIC GROUPS, USEFUL AS ANTI-ULCER OR ANTI-SECRETORY AGENTS

[75] Inventor: Roger Crossley, Reading, England

[73] Assignee: John Wyeth & Brother Limited, Maidenhead, England

[21] Appl. No.: 807,886

[22] Filed: Dec. 11, 1985

Related U.S. Application Data

[63] Continuation-in-part of Ser. No. 707,337, Mar. 1, 1985, abandoned, which is a continuation-in-part of Ser. No. 677,790, Dec. 4, 1984, abandoned.

[30] Foreign Application Priority Data

Dec. 16, 1983 [GB] United Kingdom ............... 8333580
Sep. 28, 1984 [GB] United Kingdom ............... 8424607
Dec. 14, 1984 [GB] United Kingdom ............... 8431637

[51] Int. Cl.[4] ............... C07D 471/04; C07D 215/12; C07D 215/16; C07D 487/04; A61K 31/40; A61K 31/435; A61K 31/44; A61K 31/47

[52] U.S. Cl. ................... 514/292; 514/214; 514/269; 514/274; 514/256; 514/322; 514/373; 514/312; 514/338; 514/365; 514/367; 514/314; 514/369; 514/372; 514/387; 546/84; 546/153; 546/155; 546/157; 546/199; 546/271; 546/165; 546/166; 540/579; 548/305; 548/213; 548/214; 548/181; 548/159; 548/209; 548/210; 548/207; 544/300; 544/310; 544/315; 544/318; 544/319; 544/333; 544/298

[58] Field of Search ............... 546/84, 152, 153, 155, 546/157, 199, 271, 165, 166; 544/300, 310, 315, 318, 319, 333, 298; 540/579; 548/305, 213, 214, 181, 159, 209, 210, 207; 514/292, 214, 269, 274, 256, 322, 373, 312, 338, 365, 367, 314, 369, 372, 387

[56] References Cited

FOREIGN PATENT DOCUMENTS 2069492 2/1981 United Kingdom ............... 546/271

OTHER PUBLICATIONS

Goodman, et al., The Pharmacological Basis of Therapeutics, 6 Ed, p. 28.

Primary Examiner—Henry R. Jiles
Assistant Examiner—J. Richter
Attorney, Agent, or Firm—George Tarnowski

[57] ABSTRACT

The invention provides novel imidazoquinolines, processes for their preparation and pharmaceutical compositions containing them. The compounds have Formula I

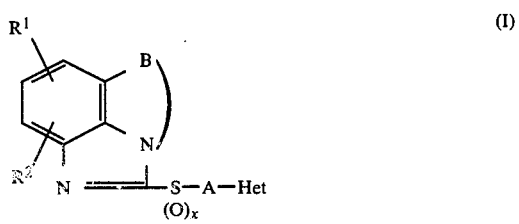

wherein
A is a $C_1$-$C_4$ straight or branched alkylene chain which may be saturated or unsaturated,
B is a $C_2$-$C_4$ straight or branched alkylene chain which may be saturated or unsaturated,
$R^1$ and $R^2$ are the same or different and are hydrogen, $C_{1-6}$ alkyl, $C_{1-6}$ alkoxy, $C_{1-6}$ alkoxyalkyl, $C_{1-6}$ hydroxyalkyl, hydroxy, halogen, nitro, carboxy, carboxylic lower alkyl ester, carbamoyl, carbamoyloxy, cyano, loweralkanoyl, lower alkanoylamino or trifluoromethyl, Het is a heterocyclic group chosen from imidazolyl, imidazolinyl, benzimidazolyl, thiazolyl, thiazolinyl, quinolyl, piperidyl, pryidyl, benzothiazoly and pyrimidyl, any of which heterocyclic groups may be substituted, and x is 0 or 1, and pharmaceutically acceptable salts thereof.

The compounds are anti-ulcer/anti-secretory agents.

17 Claims, No Drawings

IMIDAZOQUINOLINES CONTAINING OTHER HETEROCYCLIC GROUPS, USEFUL AS ANTI-ULCER OR ANTI-SECRETORY AGENTS

The invention relates to novel imidazoquinoline derivatives useful for the treatment of ulcers or hypersecretion in mammals, to processes for their preparation and to pharmaceutical compositions containing the novel compounds. This application is a continuation-in-part of Application Serial No. 707,337 filed Mar. 1, 1985, now abandoned which in turn is a continuation-in-part of Ser. No. 677,790 filed Dec. 4, 1984, now abandoned.

In our GB Patent Specification No. 2069492A we have described inter alia phenylsulphinylalkylpyridines which are useful in the treatment of ulcers or hypersecretion in mammals. We have now found that by modifying the molecule to replace the phenyl group by an imidazoquinoline group novel compounds are obtained which have one or more of the following activities, anti-ulcer, anti-secretory or $H^+/K^+$ ATPase inhibitory activity. The pyridyl group can also be replaced by other heterocyclic groups as detailed below.

The invention provides a compound of formula I

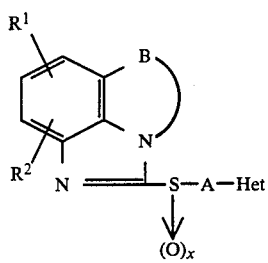
(I)

wherein

A is a $C_1$–$C_4$ straight or branched alkylene chain which may be saturated or unsaturated, B is a $C_2$–$C_4$ straight or branch alkylene chain which may be saturated or unsaturated, $R^1$ and $R^2$ are the same or different and are hydrogen, alkyl, alkoxy, alkoxyalkyl, hydroxyalkyl, hydroxy, halogen, nitro, carboxy, carboxylic loweralkyl ester, carbamoyl, carbamoyloxy, loweralkanoylamino such as acetamino, cyano, loweralkanoyl or trifluoromethyl, Het is a heterocyclic group chosen from imidazolyl, imidazolinyl, benzimidazolyl, thiazolyl, thiazolinyl, quinolyl, piperidyl, pyridyl, benzothiazolyl and pyrimidyl, any of which heterocyclic groups may be substituted, and x is 0 or 1, and pharmaceutically acceptable salts thereof.

Examples of A are $CH_2$, $CH(CH_3)$, $CH(CH_3)CH_2$, $CH_2CH_2$, $CH_2CH_2CH_2$, $CH=CH$, and $CH=CHCH_2$. Preferably A is $CH_2$.

B may be for example $CH_2CH_2$, $CH(CH_3)CH_2$, $CH_2CH_2CH_2$, $CH=CH$, $CH=CHCH_2$ or $(CH_2)_4$.

The group Het may be mono or polysubstituted but is preferably mono or disubstituted by any of the following; halogen, $C_{1-6}$ alkoxy, $C_{7-12}$ aralkoxy, hydroxy, $C_{1-6}$ hydroxyalkyl, $C_{1-6}$ alkoxyalkyl, trifluoromethyl, $C_{1-6}$ alkyl, phenyl or $C_{7-12}$ aralkyl or disubstituted by a loweralkylene dioxy radical of 1 to 6 carbon atoms. The group Het is joined via a carbon-carbon bond to group A at the 2-, 3- or 4-position of the heterocyclic ring. The group Het is preferably joined at the 2-position.

In this specification an alkyl group is preferably lower alkyl i.e. of 1 to 6 carbon atoms e.g. methyl, ethyl, n-propyl, isopropyl, n-butyl, s-butyl, t-butyl, n-pentyl or n-hexyl. An alkoxy group is preferably lower alkoxy in which the alkyl portion is as defined for a lower alkyl group. A carboxylic alkyl ester group is preferably lower alkoxy carbonyl e.g. methoxycarbonyl, ethoxycarbonyl, propoxycarbonyl etc. Whenever the term "lower alkyl" or "lower alkoxy" is used as part of another group e.g. arylloweralkyl, the lower alkyl or lower alkoxy portion has 1 to 6 carbon atoms unless otherwise stated. A lower alkanoyl group is one in which the alkyl portion has 1 to 6 carbon atoms, e.g. acetyl, propionyl, butyryl etc. An aralkyl radical is preferably phenylloweralkyl e.g. benzyl, phenethyl or phenpropyl. A phenyl group or phenyl portion of another group such as phenalkyl may be substituted e.g. by any of the substituents mentioned for the group Het.

Preferably an aralkyl group is phenylalkyl of 7–12 carbon atoms. A particularly preferred group of compounds within the scope of formula I are those in which Het is pyridyl, e.g. 2-pyridyl, which may be substituted by any of the substituents described for Het, but phenyl or substituted phenyl are particularly preferred substituents especially when n is 0. Lower alkyl substituents are also of interest. These compounds have especially interesting anti-secretory activity as measured by their ability to inhibit the highly specific proton transporting enzyme $H^+/K^+$ ATPase.

A particularly preferred group of compounds may be represented by formula (Ia)

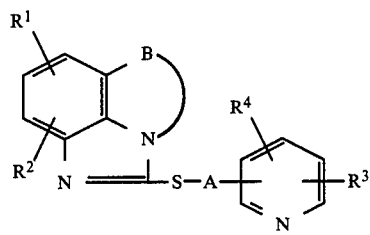
(Ia)

wherein A, $R^1$ and $R^2$ are as defined in connection with formula I above, $R^3$ and $R^4$ are the same or different and are hydrogen, lower alkyl or phenyl which may be substituted by any of the substituents described for Het, and one of $R^3$ and $R^4$ is other than hydrogen, and pharmaceutically acceptable salts thereof. The pharmaceutically acceptable salts are preferably acid addition salts.

The acid addition salts of compounds of formula I or Ia may be of any pharmaceutically acceptable organic or inorganic acid e.g. hydrochloric, hydrobromic, hydroiodic, phosphoric, sulphuric, nitric, citric, acetic, formic, fumaric, maleic, tartaric, embonic, malonic, alkylsulphonic, e.g. methanesulphonic, arylsulphonic, e.g. p-toluene sulphonic acids.

The invention includes methods of preparing the compounds of formula I.

The compounds of formula I, wherein x is 1, i.e. the sulphinyl compounds may be prepared by oxidising a corresponding compound of formula I where x is 0, or a pharmaceutically acceptable salt thereof, and if desired converting the product to an acid addition salt.

Oxidation may be effected by any suitable means for forming a sulphoxide from a thioether (see Kharasch, Organic Sulphur Compounds, Pergamon Press, New York, 1961, Volume 1, pages 157–159), for example by a per acid or peroxide. Examples of per acids are perbenzoic, m-chloroperbenzoic or peracetic acid. Hydrogen peroxide may also be used. Preferably an acid addition salt of compound II is used in order to prevent or minimise attack of the pyridine nitrogen by the oxidising agent.

The compounds of formula I, where x is 0, may be prepared by reacting a compound of formula II, $$\text{Het-A-Hal} \quad \text{(II)}$$

wherein Het and A are as defined above and Hal is a halogen atom especially chlorine, bromine or iodine, with a thiol of formula III, or an alkali metal salt thereof, (III) (IIIa)

wherein B, $R^1$ and $R^2$ are as defined above.

Alternatively a compound of formula IIa Het-A-SH, or an alkali metal salt thereof, may be reacted with a halide of formula IIIa wherein $R^1$, $R^2$, B and Hal are as defined above.

The starting compounds of formula II and IIa are known compounds or may be prepared by methods known for analogous compounds. The starting compounds of formula III or IIIa are known compounds described in for example J. Org. Chem. 1959, 25, 1138 or 1963, 28, 2581 or may be prepared by methods known for analogous compounds. In the above mentioned reaction the compounds of formula I may be isolated in free base form or as acid addition salts.

Further methods for preparing compounds of formula I include:

reacting a compound of formula IV (IV)

wherein $R^1$, $R^2$, A, B and x are as defined above and M is sodium, potassium or lithium with a compound of formula $$\text{Het-Q} \quad \text{(V)}$$

where Het is as defined above and Q is a leaving group such as a reactive esterified hydroxy group or halogen.

The compounds of formula IV and V are known compounds or may be prepared by methods known for analogous compounds.

The reactive esterified hydroxy group is preferably an hydroxy group esterified with an organic sulphonic acid e.g. benzene sulphonic acid or p-toluene sulphonic acid.

The compounds of formula I and their pharmaceutically acceptable salts, possess anti-ulcer and/or antisecretory activity as measured by standard test procedures and accordingly are useful for the treatment of ulcers or hypersecretion in mammals. The compounds of formula I where x is 0 and their pharmaceutically acceptable salts are also intermediates for the corresponding compounds where x is 1.

Anti-ulcer activity was determined by the stress-induced erosion test of Senay and Levine, Proc. Soc. Exp. Biol. Med., 124, 1221-3 (1967).

Anti-secretory activity was demonstrated by the test of H. Shay, D. Sun and H. Gruenstein, Gastroenterology, 1954, 26, 903-13 as exemplified by Beattie et al, J. Med. Chem. 20, 714 (1977).

Compounds of formula I were also tested for antisecretory activity by their ability to inhibit the highly specific proton transporting enzyme $H^+/K^+$ ATPase.

Potential $H^+/K^+$ ATPase inhibitors are evaluated by a technique involving the measurement of aminopyrine accumulation in rabbit isolated gastric glands. Aminopyrine, which is a weak base, accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action, and those which reduce the response to both DBcAMP and high potassium ion concentration ($K^+$) are thought to have an intracellular site of action at the secretory surface of the parietal cell, involving the highly specific proton - transporting enzyme, $H^+/K^+$ ATPase. The following test procedure is used:

Rabbit gastric glands are isolated from gastric mucosa from the corpus region of the stomach by a method based on one described by Berglindh T., Obrink K. J., Acta Physiol. Scand. 96, 150-159 (1976). Measurement of aminopyrine uptake is carried out using a modification of the method described by Berglindh T., Hellander H. F., Obrink K. J. (ibid, 97, 401-414, 1976).

Compounds are tested at a concentration of $10^{-4}$M, initially, and in some cases at lower concentrations, for their ability to inhibit $^{14}$C-aminopyrine uptake in gastric glands, stimulated by DBcAMP and high $K^+$ respectively. Results are expressed as the % inhibition of the maximum response to the secretagogue induced by the test compound. An inhibitor of $H^+/K^+$ ATPase would be expected to reduce the response to both secretagogues.

The invention also provides pharmaceutical compositions comprising a compound of formula I as defined above wherein x is 0 or 1, or a pharmaceutically acceptable salt thereof and a pharmaceutically acceptable carrier.

The pharmaceutical formulations include solids and liquids. Any suitable carrier known in the art can be used to prepare the pharmaceutical composition. In such a composition, the carrier is generally a solid or liquid, or a mixture of a solid and a liquid.

Solid form compositions include powders, granules, tablets and capsules (e.g. hard and soft gelatin capsules). A solid carrier can be, for example, one or more substances which may also act as flavouring agents, lubricants, solubilisers, suspending agents, fillers, glidants, compression aids, binders, effervescent excipients or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 10 to 80%, preferably 25 to 75% of the active ingredient. Suitable solid carriers include, for example, calcium phosphate, magnesium stearate, talc, sugars, lactose, dextrine, starch, gelatin, cellulose, methyl cellulose, sodium carboxymethyl cellulose, polyvinylpyrrolidone, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, suspensions, emulsions, syrups and elixirs. The active ingredient, for example, can be suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral administration include water (particularly containing additives as above e.g. cellulose derivatives, preferably sodium carboxymethyl cellulose solution) alcohols (includihg monohydric alcohols and polyhydric alcohols e.g. glycerol and glycols) and their derivatives, and oils (e.g. fractionated coconut oil and arachis oil).

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders. The unit dosage form can be, for example, a capsule or tablet itself, or it can be the appropriate number of any such compositions in package form. The quantity of the active ingredient in a unit dose of composition may be varied or adjusted from 10 mg or less to 500 mg or more, according to the particular need.

The anti-ulcer compositions of the invention will be administered orally on either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In another aspect the invention provides as pharmaceutical, e.g. an anti-ulcer agent a compound of formula I, where x is 0 or 1, or a pharmaceutically acceptable salt thereof as defined above.

The invention also provides a method of treating ulcers or hypersecretion in a mammal in need of such treatment, which method comprises administering to said mammal an effective amount of a compound of formula I or a pharmaceutically acceptable salt thereof. The amount of compound I will depend on the activity of the compound and the needs of the mammal being treated. Doses may range from 0.1 to 30 mg/kg.

The following examples illustrate the invention:

EXAMPLE 1

5,6-Dihydro-2-(2-pyridylmethylthio)-4H-imidazo-[4,5,1-ij]-quinoline

A solution of 5,6-dihydro-2-mercapto-4H-imidazo-[4,5,1-ij]quinoline (1.9 g) in ethanol (30 ml) was heated to reflux and treated with 2-picolyl chloride, hydrochloride (2.5 g) and the solution was heated at reflux for 6 hours. A solid which formed on cooling was removed by filtration and dried to give the title compound as the dihydrochloride (2.8 g) mp 215° C. decomp. (Found: C, 54.5; H, 5.0; N,12.1 $C_{16}H_{16}N_3S.2HCl$ requires C, 54.1; H,5.1; N,11.8%).

EXAMPLE 2

2-(2-Pyridylmethylsulphinyl)-5,6-dihydro-4H-imidazo-[4,5,1-ij]quinoline

A solution of 5,6-dihydro-2-(2-pyridylmethylthio)-4H-imidazo-[4,5,1-ij]quinoline hydrochloride (4.0 g) in water (10 ml) was basified with sodium carbonate solution and extracted into chloroform. The extracts were dried $(MgSO)_4$ and evaporated and the residue was dissolved in methylene chloride (50 ml) and cooled to −50° C. 3-chloroperoxybenzoic acid (2 g) was added with stirring and the solution was allowed to warm to −20° C. when a further (0.5 g) of 3-chloroperoxybenzoic acid was added and the solution was kept at 6° C. for 16 hours. It was then washed ($Na_2CO_3$ solution and brine), dried ($MgSO_4$) and evaporated to give an oil which was purified by chromatography on alumina with ethyl acetate as eluent and crystallised from di-isopropylether to give the title compound as a quarterhydrate(2.1 g) mp 100°–102° C. (Found: C, 63.9; H, 5.1; N,14.0. $C_{16}H_{15}N_3OS$, $\frac{1}{4}H_2O$ requires C, 63.7; H,5.2; N,13.9%).

EXAMPLE 3

5,6-Dihydro-2-(2-(3-methylpyridyl)methylthio)-4-[H]-imidazo-[4,5,1-ij]quinoline

A stirred suspension of 5,6-dihydro-2-mercapto-[4H]-imidazo-[4,5,1-ij]quinoline (3.8 g) in ethanol (40 ml) at reflux was treated with 3-methylpicolylchloride, hydrochloride (3.6 g) and the mixture was heated for 4 hours. The solvent was removed by evaporation and the residue dissolved in water, basified with 2N NaOH and extracted with EtOAc. The extracts were dried ($MgSO_4$) and evaporated to give a solid which was recrystallised from cyclohexane to give the title compound (4.5 g, 75%) mp 106°–8° C. (Found: C, 69.3; H,5.9; N, 13.9; $C_{17}H_{17}N_3S$ requires C, 69.1; H, 5.8; N, 14.2%).

EXAMPLE 4

2-(2-Pyridylmethylthio)-4[H]-imidazo-[4,5,1-ij]quinoline

2-Picolyl chloride, hydrochloride (0.8 g, 0.005 mole) was added to a stirred solution of 2-mercapto-[4H]-imidazo[4,5,1-ij]quinoline (0.83 g, 0.004 mole) in ethanol (17 ml) at reflux. The mixture was heated at reflux for 4 hours and evaporated. The residue was dissolved in water, basified (2N NaOH) and extracted with ethyl acetate. The extracts were washed N/10 NaOH), dried ($MgSO_4$) and evaporated and the residue was recrystallised from cyclohexane to give the title compound (0.8 g, 65%) mp 109°–10° C. (Found: C, 68.95; H, 4.7; N, 14.8 $C_{16}H_{13}N_3S$ requires C, 68.8; H, 4.7; N, 15.05%).

EXAMPLE 5

5,6-Dihydro-2-(2-(3-methylpyridyl)methylsulphinyl)-[4H]-imidazo-[4,5,1-ij]quinoline To a solution of 5,6-Dihydro-2-(2-(3-methylpyridyl)methylthio)-4-[H]-imidazo-[4,5,1-ij]quinoline (1 g, 0.0034 mole) in $CH_2Cl_2$ (50 ml) was added m-chloroperoxybenzoic acid (80%) (0.72 g, 0.0034 mole) at 0° C. with stirring. The solution was stirred for 1 hour when t.l.c. ($SiO_2/Et_2O$ or EtOAc) showed starting material present and further m-chloroperoxybenzoic acid (0.1 g) was added. The solution was stirred at 0° C. for ½ hour and allowed to warm to ambient temperature, washed with saturated $Na_2CO_3$ solution, $H_2O$ and brine, dried ($MgSO_4$) and evaporated. The residue was purified by chromatography on silica with ethyl acetate as eluent followed by trituration with ethyl acetate to give the title compound (0.6 g, 57%) mp 172°–3° C. (Found: C, 65.7; H, 5.6; N, 13.2. $C_{17}H_{17}N_3OS$ requires C, 65.6; H,5.5; N,13.5%).

EXAMPLE 6

5,6-Dihydro-2-(2-(6-phenylpyridyl)methylthio)-[4H]-imidazo-[4,5,1-ij]quinoline 5,6-Dihydro-2-mercapto-[4H]imidazo-[4,5,1-ij]-quinoline (1.8 g) was suspended in ethanol (25 ml) and a solution of NaOH (0.8 g) in water (5 ml) was added. The resulting solution was treated with 6-phenylpicolyl chloride, hydrochloride (2.4 g) and the mixture was heated at reflux for 1 hour. The reaction mixture was filtered and evaporated to give an oil which was dissolved in ethyl acetate. The solution was quickly dried ($MgSO_4$) and filtered and crystals allowed to form. These were removed by filtration and dried to give the title compound (2.2 g, 62%) mp 121°–3° C. (Found: C, 74.0; H, 5.5; N, 11.8 $C_{22}H_{19}N_3S$ requires C, 73.9; H, 5.4; N, 11.8%).

EXAMPLE 7

5,6-Dihydro-2-(2-(3,5-dimethylpyridyl)methylthio)-[4H]-imidazo-[4,5,1-ij]quinoline A solution of 5,6-dihydro-2-mercapto-[4H]-imidazo-[4,5,1-ij]quinoline (1.9 g) in ethanol (30 ml), water (5 ml) and NaOH (0.4 g) was treated with 3,5-dimethylpicolyl chloride hydrochloride (1.9 g) at ambient temperature for 24 hours then at 60° C. for 24 hours. The solution was filtered and allowed to stand when crystals formed which were removed by filtration and dried to give the title compound as the hydrochloride (1.2 g, 35%) mp 195°–9° C. (Found: C, 62.0; H, 5.9; N, 11.9 $C_{18}H_{19}N_3S.HCl$ requires C, 62.5; H,5.8; N,12.15%).

EXAMPLE 8

5,6-Dihydro-2-(2-(3,5-dimethylpyridyl)methylsulphinyl-4H-imidazo[4,5,1-ij]quinoline A solution of 5,6-dihydro-2-(2-(3,5-dimethylpyridyl)methylthio)-[4H]-imidazo[4,5,1-ij]quinoline (free base) (1.25 g) in $CH_2Cl_2$ (20 ml) was treated with m-chloroperoxybenzoic acid (0.9 g) at 0° C. for 1 hour. The solution was washed ($Na_2CO_3$) dried ($MgSO_4$) and the products separated by chromatography on silica with ethyl acetate as eluent followed by recrystallisation from EtOAc-MeCN-CHCl$_3$ to give the title compound (2.6 g, 20%) mp 164°–5° C. (Found: C, 66.2; H,6.0; N,12.9 $C_{18}H_{19}N_3OS$ requires C, 66.4; H, 5.9; N, 12.9%).

EXAMPLE 9

5,6-Dihydro-2-[(2-phenylthiazol-4-yl)methylthio]-4H-imidazo[4,5,1-ij]quinoline

A solution of 5,6-dihydro-2-mercapto[4H]imidazo [4,5,1-ij]quinoline (2.04 g, 10.7 mmol) in 1 N-sodium-hydroxide (10.7 ml) and ethanol (10 ml) was treated with 4-chloromethyl-2-phenylthiazole (2.25 g, 10.7 mmol) and the resulting solution heated under reflux for 5 mins. The mixture was concentrated in vacuo and the aqueous mixture extracted with ethyl acetate (2×50 ml). The extracts were dried ($MgSO_4$) and evaporated in vacuo to give a yellow oil which crystallised on trituration with diethyl ether (50 ml) to give the title compound (3.62 g, 93%), mp 116°–118° (Found: C, 66.4; H, 5.0; N, 11.3 $C_{20}H_{17}N_3S_2$ requires C, 66.1; H, 4.7; N, 11.6%).

EXAMPLE 10

(A)

5,6-Dihydro-8-methoxy-4H-imidazo[4,5,1-ij]quinoline-2[1H]-thione

A suspension of 6-methoxy-8-nitroquinoline (20 g, 98 mmol) in methanol (200 ml) was hydrogenated over $PtO_2$ (0.5 g) at 50 p.s.i. for 2.5 hours. The solution was treated with acetic acid (11.5 ml, 200 mmol) and $PtO_2$ (0.5 g) and hydrogenated at 50 p.s.i. for 18 hours. The catalyst was removed by filtration and the solution evaporated in vacuo to give an oil. The residue was basified with 1 N-sodium hydroxide (200 ml) and the aqueous mixture extracted with diethyl ether (2×200 ml). The extracts were dried ($MgSO_4$) and evaporated in vacuo to give crude 8-amino-1,2,3,4-tetrahydro-6-methoxyquinoline as a red oil.

The oil was dissolved in methanol (100 ml) and the solution treated with $CS_2$ (10 ml, 167 mmol), heated under reflux for 18 hours, cooled to room temperature, and evaporated in vacuo to give a brown solid. The solid was dissolved in warm 1 N-sodium hydroxide (100 ml) and the cold solution washed with di-isopropyl ether (2×200 ml). The ethereal washings were extracted with 0.1 N-sodium hydroxide (100 ml). The aqueous solution and extract were combined, heated on a steambath, decolourised with activated charcoal, filtered, cooled to 0° C., and neutralised with stirring with acetic acid (10 ml). The precipitate was filtered, washed with copious amounts of water and dried in vacuo to give 5,6-dihydro-8-methoxy-4H-imidazo[4,5,1-ij]-quinoline-2[1H]-thione (18.2 g, 84%) as light brown crystals, mp 188°–192° C. (Found: C, 59.8; H, 5.5; N, 12.4 $C_{11}H_{12}N_2OS$ requires C, 60.0; H, 5.5; N, 12.7%).

(B)

5,6-Dihydro-8-methoxy-2-[(6-phenylpyridin-2-yl)-methylthio]-4H-imidazo[4,5,1-ij]quinoline 2-Chloromethyl-6-phenylpyridine hydrochloride 1.942 g, 8.1 mmol) was added to a solution of 5,6-dihydro-8-methoxy-4H-imidazo[4,5,1-ij]quinoline-2[1H]-thione (1.78 g, 8.1 mmol) in ethanol (16 ml) and 1N-sodium hydroxide (16.2 ml). The mixture was heated under reflux for 15 seconds and cooled to room temperature. The ethanol was removed by evaporation in vacuo and the aqueous mixture extracted with dichloromethane (2×150 ml). The extracts were dried ($MgSO_4$)

and evaporated in vacuo to give a brown solid which was recrystallised from MeOH to give the title compound as the quarter hydrate (2.77 g, 88%), mp 134°–135° C. (Found: C, 70.5; H, 5.8; N, 10.4; $C_{23}H_{21}N_3OS\cdot\frac{1}{4}H_2O$ requires C, 70.5; H, 5.5; N, 10.7%).

EXAMPLE 11

5,6-Dihydro-2-(quinolin-2-ylmethylthio)-4H-imidazo-4,5,1-ij]quinoline

A solution of 5,6-dihydro-4H-imidazo[4,5,1-ij]-quinoline-2(1H)-thione (2.02 g, 11.6 mmol) in ethanol (25 ml) and 1N-sodium hydroxide was treated with 2-(chloromethyl)quinoline hydrochloride (2.48 g, 11.6 mmol) heated to reflux, cooled to room temperature, and the ethanol removed by evaporation in vacuo. The aqueous mixture was filtered and the precipitate washed with water (5×50 ml), dried in vacuo, and recrystallised from cyclohexane - EtOAc to give 5,6-dihydro-2-(quinolin-2-ylmethylthio)-4H-imidazo[4,5,1-ij]quinoline (2.13 g, 55%) as yellow crystals mp 125°–126° C. (Found: C, 72.8; H, 5.3; N,12.4 $C_{20}H_{17}N_3S$ requires C, 72.5; H, 5.2; N, 12.7%).

EXAMPLE 12

5,6-Dihydro-2-(3-pyridylmethylthio)-4H-imidazo[4,5,1-ij]quinoline

Following the procedure of Example 1, 5,6-dihydro-2-mercapto-4H-imidazo[4,5,1-ij]quinoline (1.9 g) in ethanol (30 ml) is treated with 3-picolyl chloride, hydrochloride (2.5 g) to obtain the title compound as the dihydrochloride.

EXAMPLE 13

5,6-Dihydro-2-(4-pyridylmethlthio-4H-imdazo[4,5,1-ij]-quinoline

Following the procedure of Example 1, 5,6-dihydro-2-mercapto-4H-imidazo[4,5,1-ij]quinoline (1.9 g) in ethanol (30 ml) is treated with 4-picolyl chloride, hydrochloride (2.5 g) to obtain the title compound as the hydrochloride.

EXAMPLE 14

Following the procedure of Example 1 the following compounds are prepared.

Starting Materials

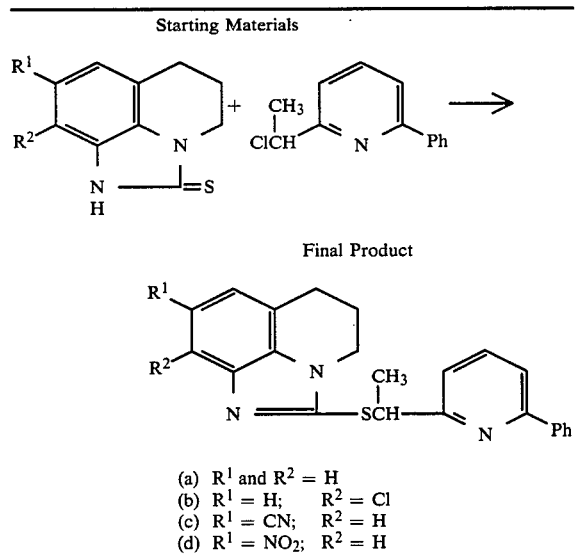

(a) $R^1$ and $R^2$ = H
(b) $R^1$ = H;   $R^2$ = Cl
(c) $R^1$ = CN;  $R^2$ = H
(d) $R^1$ = NO_2; $R^2$ = H
(e) $R^1$ = Cl;  $R^2$ = H

EXAMPLE 15

Following the procedure of Example 1 the following compounds are prepared.

Starting Materials

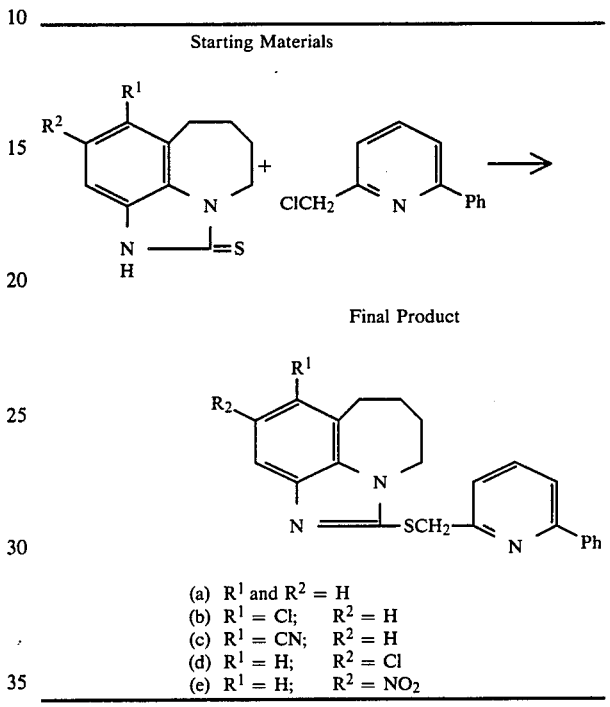

(a) $R^1$ and $R^2$ = H
(b) $R^1$ = Cl;  $R^2$ = H
(c) $R^1$ = CN;  $R^2$ = H
(d) $R^1$ = H;   $R^2$ = Cl
(e) $R^1$ = H;   $R^2$ = NO_2

EXAMPLE 16

Following the procedure of Example 2 the following sulphinyl compounds are prepared.

Starting Materials

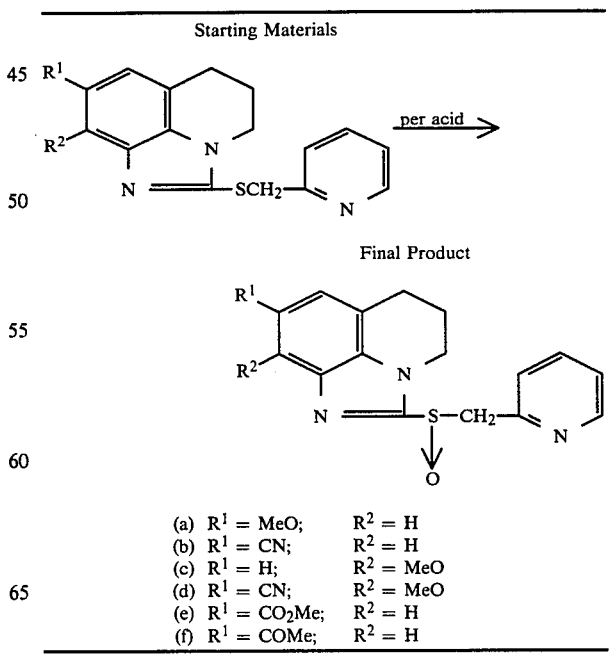

(a) $R^1$ = MeO;    $R^2$ = H
(b) $R^1$ = CN;     $R^2$ = H
(c) $R^1$ = H;      $R^2$ = MeO
(d) $R^1$ = CN;     $R^2$ = MeO
(e) $R^1$ = CO_2Me; $R^2$ = H
(f) $R^1$ = COMe;   $R^2$ = H

EXAMPLE 17

Following the procedure of Example 9 the following compounds are prepared.

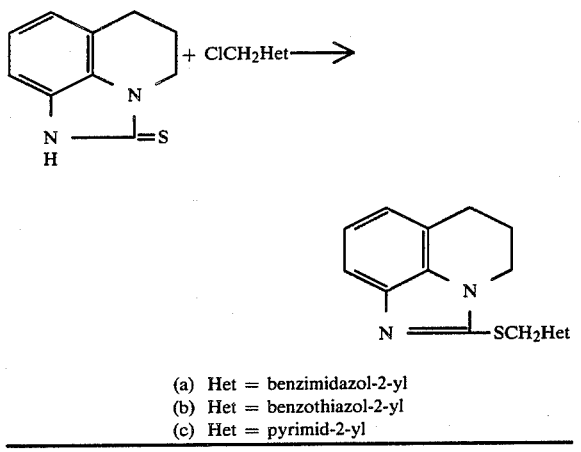

(a) Het = benzimidazol-2-yl
(b) Het = benzothiazol-2-yl
(c) Het = pyrimid-2-yl

EXAMPLE 18

Following the procedure of Example 2 the following sulphinyl compounds are prepared.

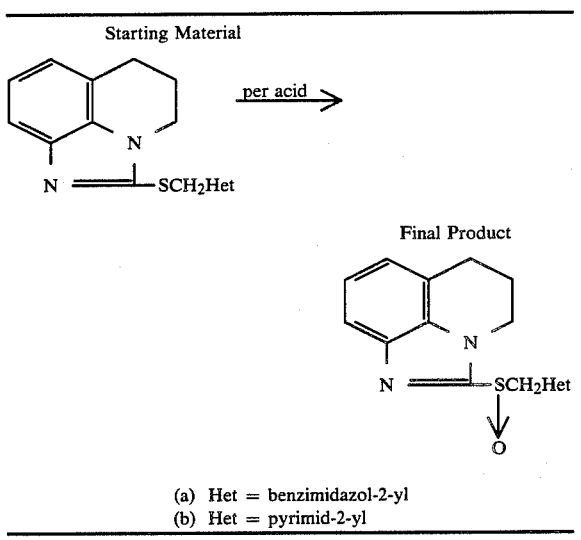

(a) Het = benzimidazol-2-yl
(b) Het = pyrimid-2-yl

EXAMPLE 19

5,6-Dihydro-8-methoxy-2-(quinolin-2-ylmethylthio)-4H-imidazo-[4,5,1-ij]quinoline 2-Chloromethylquinoline hydrochloride (0.845 g, 4.0 mmol) was added to a solution of 5,6-dihydro-8-methoxy-4H-imidazo[4,5,1-ij]quinoline-2(1H)-thione (0.871 g, 4.0 mmol) in 1 N-NaOH (8 ml) and EtOH (8 ml). The mixture was heated to reflux, cooled to room temperature, concentrated in vacuo, and the aqueous residue extracted with $CH_2Cl_2$ (50 ml). The extract was washed with 1NNaOH (2×30 ml), and brine (20 ml), dried ($MgSO_4$), and evaporated in vacuo to give an oil which was purified by chromatography ($SiO_2$, $Et_2O$) and trituration with $Et_2O$-petrol ether to give the title compound (0.885 g, 62%) as yellow crystals, mp 89°–91° C. (Found: C,70.1; H,5.4; N,11.4; $C_{21}H_{19}N_3OS$ requires C,69.8; H,5.3; N,11.6%).

EXAMPLE 20

5,6-Dihydro-8-methoxy-2-(4-pyridylmethylthio)-4H-imidazo[4,5,1-ij]quinoline

To a suspension of 5,6-dihydro-8-methoxy-2-mercapto-4H-imidazo[4,5,1-ij]quinoline (2.2 g) in ethanol was added 4-picolyl chloride HCl (1.68 g) and the mixture was stirred at ambient temperature for 16 hours and at reflux for 2 hours. The solvent was removed by evaporation and the residue dissolved in water. The solution was washed with EtOAc and then basified (aqueous NaOH) and extracted with $CHCl_3$. Following short column chromatography ($SiO_2/CHCl_3$) the residue was crystallised from EtOAc to give the title compound (1.45 g, 43%) mp 99°–101° C. (Found: C,65.55; H,5.6; N,13.8. $C_{17}H_{17}N_3OS$, requires C,65.6; H,5.5; N,13.5%).

EXAMPLE 21

5,6-Dihydro-2-(4-pyridylmethylthio)-4H-imidazo[4,5,1-ij]-quinoline

To a suspension of 5,6-dihydro-2-mercapto-4H-imidazo [4,5,1-ij]quinoline (1.9 g) in ethanol was added 4-picolyl chloride HCl (1.68 g) and the mixture was stirred at ambient temperature for 16 hours and at reflux for 2 hours. The solvent was removed by evaporation and the residue dissolved in water. The solution was washed with EtOAc and then basified (aqueous NaOH) and extracted with $CHCl_3$. Following short column chromatography ($SiO_2/CHCl_3$) the residue was crystallised from EtOAc to give the title compound (1.25 g, 44%). mp 105°–7° C. (Found: C,68.20; H,5.50; N,15.30. $C_{16}H_{15}N_3S$ requires C,68.30; H,5.40; N,14.90).

EXAMPLE 22

Following the procedure of Example 1 the following compounds are prepared.

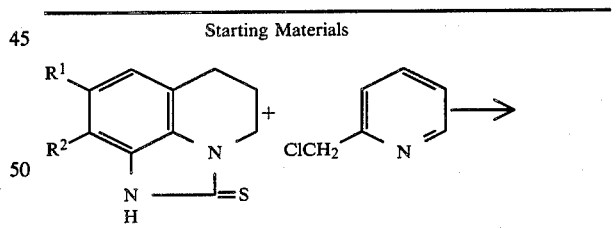

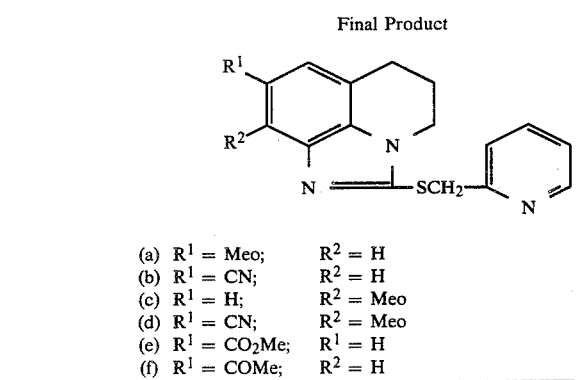

(a) $R^1$ = Meo;   $R^2$ = H
(b) $R^1$ = CN;    $R^2$ = H
(c) $R^1$ = H;     $R^2$ = Meo
(d) $R^1$ = CN;    $R^2$ = Meo
(e) $R^1$ = $CO_2Me$;  $R^1$ = H
(f) $R^1$ = COMe;  $R^2$ = H

Pharmacological Test Results

| Compound | Stress Induced Erosion Senay & Levine | | Anti-Secretory (Shay et al) | | % Inhibition to Stimulation by | |
|---|---|---|---|---|---|---|
| | Dose mg/kg | Inhibition | Dose mg/kg | % Change in volume | DBcAMP at $10^{-4}$ | $K^+$ at $10^{-4}$ |
| Example 1 | 100 | 69 | 30 | N/A | 34 | −215 |
| Example 2 | 100 | 60 | 30 | N/A | 97 | 65 |
| Example 3 | 100 | 68 | 30 | N/A | N/A | −109 |
| Example 4 | | N/T | 30 | N/A | 16.7 | 35.5 |
| Example 5 | | N/T | 30 | N/A | 66 | N/A |
| Example 6 | 100 | 58% | 30 | N/A | 36 | 182 |
| Example 7 | 100 | N/A | 30 | N/A | 70 | 74 |
| Example 8 | | N/T | 30 | N/A | 48 | N/A |
| Example 9 | 100 | N/A | 30 | N/A | 75 | 122 |
| Example 10B | 100 | N/A | 30 | N/A | 98 | 136 |
| Example 11 | 100 | N/A | 30 | 22 | 62 | 147 |
| Example 19 | 100 | N/A | 30 | N/A | 70 | 124 |
| Example 20 | 30 | N/A | 30 | N/A | 68 | N/A |
| Example 21 | 30 | N/A | 30 | N/A | 66 | N/A |

N/A = No significant activity
N/T = Not tested

What is claimed is:

1. A compound of formula I

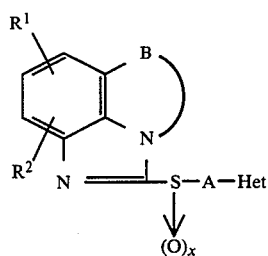

wherein
A is a $C_1$–$C_4$ straight or branched carbon chain which may be saturated or unsaturated,
B is a $C_2$–$C_4$ straight or branched carbon chain which may be saturated or unsaturated,
$R^1$ and $R^2$ are the same or different and are hydrogen, $C_1$–$C_6$ alkyl, $C_1$–$C_6$ alkoxyalkyl, $C_1$–$C_6$ hydroxyalkyl, hydroxy, halogen, nitro, carboxy, carboxylic lower alkyl ester, carbamoyl, carbamoyloxy, cyano, lower alkanoyl, lower alkanoylamino or trifluromethyl, Het is a heterocyclic group joined via a carbon-carbon bond to A at the 2-, 3- or 4-position of the heterocyclic ring and chosen from imidazolyl, imidazolinyl, benzimidazolyl, thiazolyl, thiazolinyl, quinolyl, piperidyl, pyridyl, benzothiazolyl and pyrimidyl, any of which heterocyclic groups may be substituted by one or more of the following: halogen, $C_{1-6}$ alkoxy, $C_{7-12}$ phenylalkoxy, hydroxy, $C_{1-6}$ hydroxylalkyl, $C_{1-6}$ alkoxyalkyl, trifluoromethyl, $C_{1-6}$ alkyl, phenyl or $C_{7-12}$ phenylalkyl or disubstituted by a lower alkylene dioxy radical of 1 to 6 carbon atoms, and x is 0 or 1, or pharmaceutically acceptable salts thereof.

2. A compound as claimed in claim 1 wherein Het is pyridyl, quinolyl or thiazolyl which may be substituted by one or more of the following: halogen, $C_1$–$C_6$ alkoxy, $C_7$–$C_{12}$ phenylalkoxy, hydroxy, $C_1$–$C_6$ hydroxy alkyl, $C_1$–$C_6$ alkoxyalkyl, trifluoromethyl, $C_1$–$C_6$ alkyl, phenyl or $C_7$–$C_{12}$ phenylalkyl, or disubstituted by loweralkylenedioxy of 1 to 6 carbon atoms.

3. A compound as claimed in claim 1, wherein Het is joined at the 2-position.

4. A compound of formula Ia

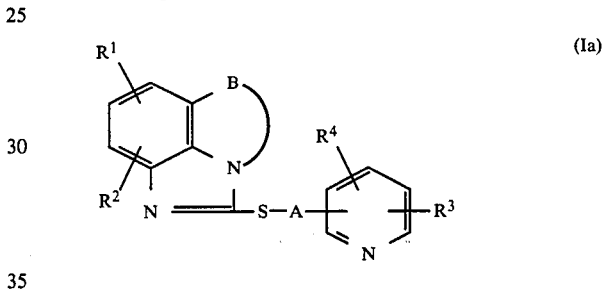

(Ia)

wherein A, $R^1$ and $R^2$ are as defined in claim 1 in connection with formula I, $R^3$ and $R^4$ are the same or different and are hydrogen, loweralkyl or phenyl which may be substituted by any of the substituents described for Het in claim 1, and one of $R^3$ and $R^4$ is other than hydrogen, or pharmaceutically acceptable salts thereof.

5. A compound as claimed in claim 1 wherein A is $CH_2$.

6. A compound as claimed in claim 1 wherein $R^1$ and $R^2$ are selected from hydrogen, loweralkyl and loweralkoxy.

7. A compound as claimed in claim 1, wherein Het is 2-(6-phenyl-pyridyl).

8. A compound selected from 5,6-dihydro-2-(2-pyridylmethylthio)-4H-imidazo[4,5,1-ij]-quinoline or a pharmaceutically acceptable salt thereof, 2-(2-pyridylmethylsulphinyl)-5,6-dihydro-4H-imidazo-[4,5,1-ij]quinoline or a pharmaceutically acceptable salt thereof, 5,6-dihydro-2-(2-(3-methylpyridyl)methylthio)-4[H]-imidazo[4,5,1-ij]quinoline or a pharmaceutically acceptable salt thereof, 2-(2-pyridylmethylthio)-4[H]-imidazo[4,5,1-ij]quinoline or a pharmaceutically acceptable salt thereof, 5,6-dihydro-2-(2-(3-methylpyridyl)methylsulphinyl)-[4H]-imidazo[4,5,1-ij]quinoline or a pharmaceutically acceptable salt thereof, 5,6-dihydro-2-(2-(6-phenylpyridyl)methylthio)-[4H]-imidazo[4,5,1-ij]quinoline or a pharmaceutically acceptable salt thereof, 5,6-dihydro-2-(2-(3,5-dimethylpyridyl)methylthio)-[4H]-imidazo[4,5,1-ij]quinoline or a pharmaceutically acceptable salt thereof, 5,6-dihydro-2-(2-(3,5-dimethylpyridyl)methylsulphinyl)-4H-imidazo[4,5,1-ij]quinoline or a pharmaceutically acceptable salt thereof, 9. 5,6-Dihydro-2-(2-quinolylmethylthio)-4H-imidazo[4,5,1ij]-quinoline or a pharmaceutically acceptable salt thereof.

10. 5,6-Dihydro-2-(6-phenyl-2-pyridylmethylthio)-4H-8-methoxyimidazo[4,5,1-ij]quinoline or a pharmaceutically acceptable salt thereof.

11. 5,6-Dihydro-2-[(2-phenylthiazol-4-yl)methylthio]-4H-imidazo[4,5,1-ij]quinoline or a pharmaceutically acceptable salt thereof.

12. A compound as claimed in claim 1, which is 5,6-dihydro-2-(3-pyridylmethylthio)-4H-imidazo[4,5,1-ij]quinoline or a pharmaceutically acceptable salt thereof.

13. A compound as claimed in claim 1, which is 5,6-dihydro-2-(4-pyridylmethylthio)-4H-imidazo[4,5,1-ij]quinoline or a pharmaceutically acceptable salt thereof or 5,6-dihydro-8-methoxy-2-(4-pyridylmethylthio)-4H-imidazo[4,5,1-ij]-quinoline or a pharmaceutically acceptable salt thereof.

14. A compound as claimed in claim 1, which is 5,6-dihydro-8-methoxy-2-(quinolin-2-ylmethylthio)-4H-imidazo[4,5,1-ij]quinoline or a pharmaceutically acceptable salt thereof.

15. A method of treating ulcers or hypersecretion in a mammal in need of such treatment, which method comprises administering to said mammal an anti-ulcer effective amount of a compound as claimed in claim 1.

16. A pharmaceutical composition for use in treating ulcers or hypersecretion comprising an anti-ulcer effective amount of a compound as claimed in claim 1, and a pharmaceutically acceptable carrier.

17. A pharmaceutical composition for use in treating ulcers or hypersecretion as claimed in claim 16 in unit dosage form.

* * * * *